United States Patent [19]
Ellingson et al.

[11] Patent Number: 5,689,332
[45] Date of Patent: Nov. 18, 1997

[54] AUTOMATED REAL-TIME DETECTION OF DEFECTS DURING MACHINING OF CERAMICS

[75] Inventors: William A. Ellingson, Naperville; Jiangang Sun, Westmont, both of Ill.

[73] Assignee: The University of Chicago, Chicago, Ill.

[21] Appl. No.: 713,833

[22] Filed: Sep. 13, 1996

[51] Int. Cl.$^6$ ............................. G01N 21/00; G01J 4/00
[52] U.S. Cl. .................... 356/237; 356/369; 250/225; 250/559.46
[58] Field of Search ................... 356/237, 369; 250/559.45, 559.42, 559.09, 559.46, 559.48, 225

[56] References Cited

U.S. PATENT DOCUMENTS

| | | | |
|---|---|---|---|
| 3,993,976 | 11/1976 | Ginsburg | 340/146.3 |
| 4,314,017 | 2/1982 | Takahashi | 430/109 |
| 4,314,763 | 2/1982 | Steigmeier | 356/237 |
| 4,352,016 | 9/1982 | Duffy | 250/358.1 |
| 4,391,524 | 7/1983 | Steigmeier | 356/338 |
| 4,933,537 | 6/1990 | Silva | 250/572 |
| 4,978,862 | 12/1990 | Silva | 250/572 |
| 5,032,734 | 7/1991 | Orazio, Jr. | 250/572 |
| 5,070,045 | 12/1991 | Comte | 501/4 |
| 5,196,716 | 3/1993 | Moriya | 250/572 |
| 5,426,506 | 6/1995 | Ellingson | 356/369 |

OTHER PUBLICATIONS

"Analytical Calculations and Numerical Simulations of Box–Car Thermal Wave Imges of Planar Subsurface Scatterers," by D.J. Crowther et al., Wayne State University, *Review of Progress in Quantitative Nondestructive Evaluation*, vol. 11A, pp. 417–423, 1992.

*Primary Examiner*—Frank G. Font
*Assistant Examiner*—Amanda Merlino
*Attorney, Agent, or Firm*—Emrich & Dithmar

[57] ABSTRACT

Apparatus for the automated real-time detection and classification of defects during the machining of ceramic components employs an elastic optical scattering technique using polarized laser light. A ceramic specimen is continuously moved while being machined. Polarized laser light is directed onto the ceramic specimen surface at a fixed position just aft of the machining tool for examination of the newly machined surface. Any foreign material near the location of the laser light on the ceramic specimen is cleared by an air blast. As the specimen is moved, its surface is continuously scanned by the polarized laser light beam to provide a two-dimensional image presented in real-time on a video display unit, with the motion of the ceramic specimen synchronized with the data acquisition speed. By storing known "feature masks" representing various surface and sub-surface defects and comparing measured defects with the stored feature masks, detected defects may be automatically characterized. Using multiple detectors, various types of defects may be detected and classified.

15 Claims, 6 Drawing Sheets

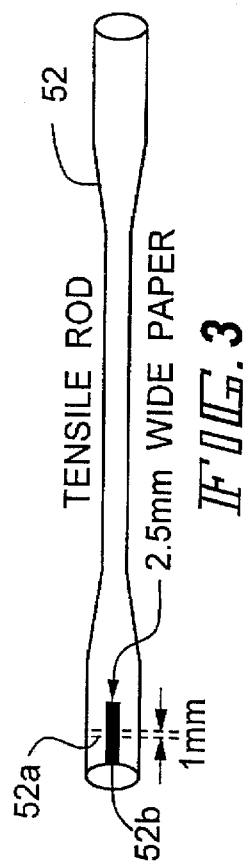
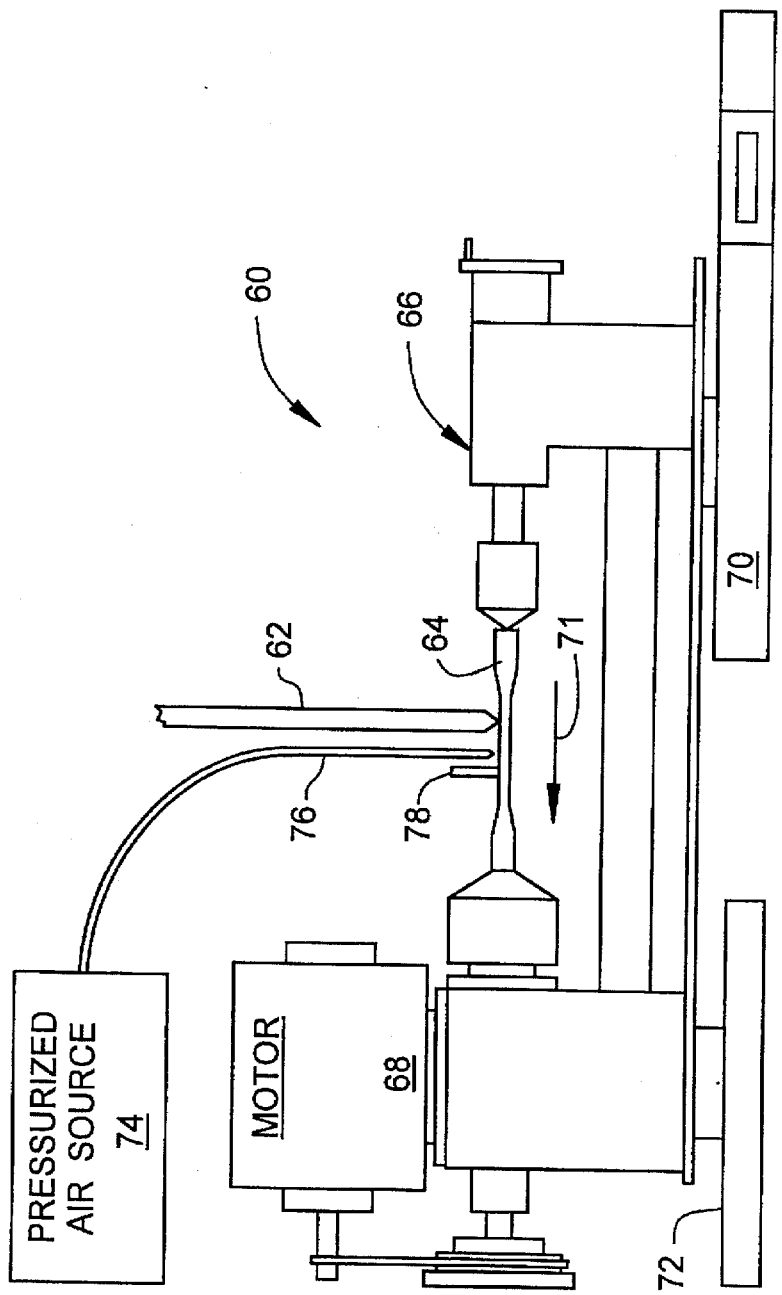

SUM IMAGE
(LATERAL DEFECT)

RATIO IMAGE
(MEDIAN DEFECT)

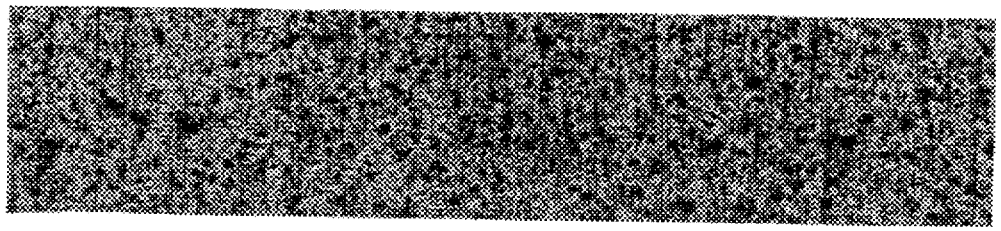
ELASTIC OPTICAL SCATTER RATIO IMAGE OF COUPON 10102
RATIO IMAGE
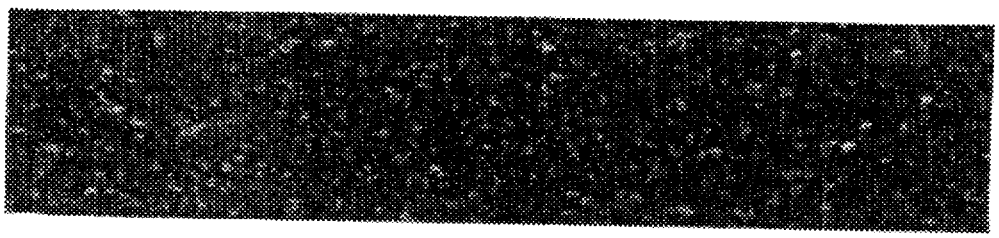
ELASTIC OPTICAL SCATTER RATIO IMAGE OF COUPON 10102
SUM IMAGE

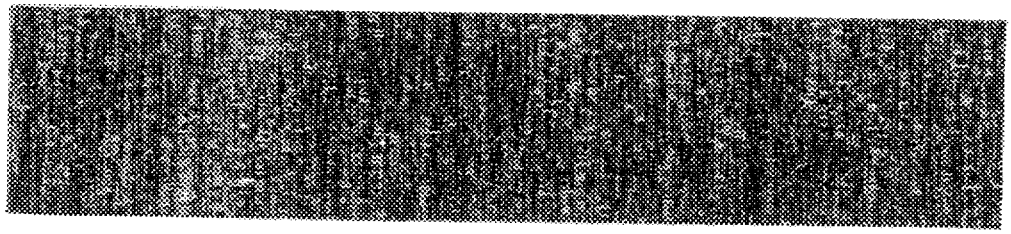
FIG. 7a SURFACE SCAN IMAGE OF COUPON 10202
RATIO IMAGE
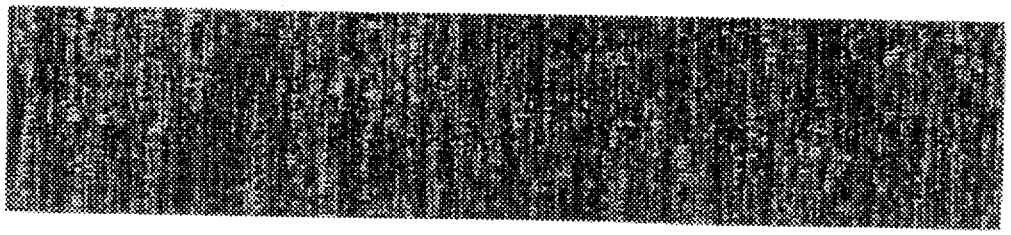
FIG. 7b SURFACE SCAN IMAGE OF COUPON 10202
SUM IMAGE

AUTOMATED REAL-TIME DETECTION OF DEFECTS DURING MACHINING OF CERAMICS

CONTRACTUAL ORIGIN OF THE INVENTION

The United States Government has rights in this invention pursuant to Contract No. W-31-109-ENG-38 between the U.S. Department of Energy and The University of Chicago representing Argonne National Laboratory.

FIELD OF THE INVENTION

This invention relates generally to the detection of defects during the machining of ceramics and is particularly directed to the automated, real-time detection and classification of surface and near-surface defects in ceramics during the machining process.

BACKGROUND OF THE INVENTION

Because of their mechanical and physical properties, such as higher stiffness, corrosion and wear resistance, and greater thermal stability, ceramics such as silicon nitride ($Si_3N_4$) ceramics are considered the materials of choice to replace steels in such applications as contact rolling elements, e.g. bearings, where stiffness and wear resistance play a key roll. There is also interest in these types of ceramics for high-temperature turbine bearing components where increased thermal stability is critical. For such applications, the most critical portions of the ceramic component, i.e., those with the highest stress during operation, are the surface or near-surface (usually to depths of <200 µm) regions. The most common types of defects found in these critical regions are mechanical in nature, such as cracks, spalls, inclusions, voids, etc., and can be either machining or operation induced.

During the machining of ceramics, the material encounters high stresses and temperatures and as a result may become broken and/or deformed. This causes tensile stresses which results in the formation of radial, lateral and longitudinal cracks. Neither radial nor lateral cracks are thought to significantly reduce the strength of the ceramic. The longitudinal (sometimes called median) cracks are thought to cause the greatest strength reduction.

Because the smallest critical defects are located on or just beneath the surface, traditional non-destructive examination (NDE) methods such as radiography, including high resolution X-ray computer tomography (CT), and ultrasonics, are not well suited for defect detection. High resolution X-ray CT is mainly sensitive to interior (bulk) defects and is therefore relatively insensitive to surface/near-surface defects. Ultrasonics can be highly sensitive to the surface/near-surface region through the use of Surface Acoustic Waves (SAWs). To provide sufficient spatial resolution, a scanning SAW microscope is needed, but this instrument is primarily intended for flat surfaces, not the curvatures and complex geometries associated with ceramic components. In addition, determination of microstructural anisotropy requires even more time and effort.

Some of the most critical defects are thus located on or just beneath the surface and originate when the manufactured part undergoes machining. Machining of engineering ceramic surfaces is conducted by a variety of material removal processes. The finish of the machined surfaces depends upon the end use of the component and in turn this directs the type of machining operation used. It is well known that a high cost value is added to the final product by machining operations. Any machining induced damage which causes part rejection is to be avoided as early in the process as possible. An on-line method for determining the amount of surface and sub-surface damage imparted to a ceramic is therefore desired. Using an on-line detection method, machine tool feed rates and contact pressures can be optimized during machining to obtain the highest material removal rates without adversely affecting the mechanical or tribological properties of the ceramic.

The present invention addresses the aforementioned limitations of the prior art by providing an arrangement for the automatic real-time detection and classification of defects during the machining of ceramic components. By directing polarized laser light onto the ceramic component at a fixed position on the ceramic component just aft of the machining tool and observing the elastic scattering of the light using a plurality of detectors, various types of surface and near-surface defects can be detected, measured and classified.

OBJECTS AND SUMMARY OF THE INVENTION

Accordingly, it is an object of the present invention to detect defects in a machined ceramic body during the machining process.

It is another object of the present invention to provide for the automated, real-time detection of surface and near-surface defects during the machining operation of ceramics.

Yet another object of the present invention is to detect, classify and record surface and near-surface defects in a machined ceramic body in real-time as the ceramic body is being machined using an automated system employing an elastic optical scattering technique with polarized light programmed to follow the machining operation and focus on the newly exposed machined surfaces.

A further object of the present invention is to provide an arrangement for detecting surface and near-surface defects in a machined ceramic component during the machining process which is capable of distinguishing between different types of defects and comparing the detected defect with various standard defects to allow for automatic rejection of defective ceramic components.

This invention contemplates apparatus for the detection and display of surface and near-surface defects in a ceramic body during machining of a surface of the ceramic body, wherein various types of defects may be introduced in a surface and near-surface portion of the ceramic body during machining, the apparatus comprising: a light source for providing a polarized laser beam; an optical arrangement for focussing and directing the polarized laser beam onto the surface of the ceramic body; a displacement mechanism for providing relative displacement between the ceramic body and the light source whereby the polarized laser beam scans the surface of the ceramic body; a plurality of detectors responsive to the polarized laser beam reflected from the surface and near-surface portions of the ceramic body for detecting various types of surface and near-surface defects in the ceramic body; and a video display coupled to the plurality of detectors for providing a video image of the various types of surface and near-surface defects in the ceramic body.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings where like reference characters identify like elements throughout the various figures, in which:

FIG. 2 is a simplified schematic diagram of an arrangement for the machining of a ceramic tensile rod for use with the automated real-time defect detection system of the present invention;

FIG. 3 is a side elevation view of a ceramic tensile rod showing a portion of the rod scanned by a polarized laser beam for detecting surface and near-surface defects in the rod in accordance with the principles of the present invention;

FIGS. 6a and 6b respectively show ratio and sum elastic optical scattering images of a diamond ground $Si_3N_4$ (GS-44) coupon specimen 10102 as detected and recorded by the present invention;

FIGS. 7a and 7b respectively show ratio and sum elastic optical scattering images of a diamond ground $Si_3N_4$ (GS-44) coupon specimen 10202 as detected and recorded by the present invention.

DETAILED DESCRIPTION OF THE PREFERRED EMBODIMENT

Figure 1:
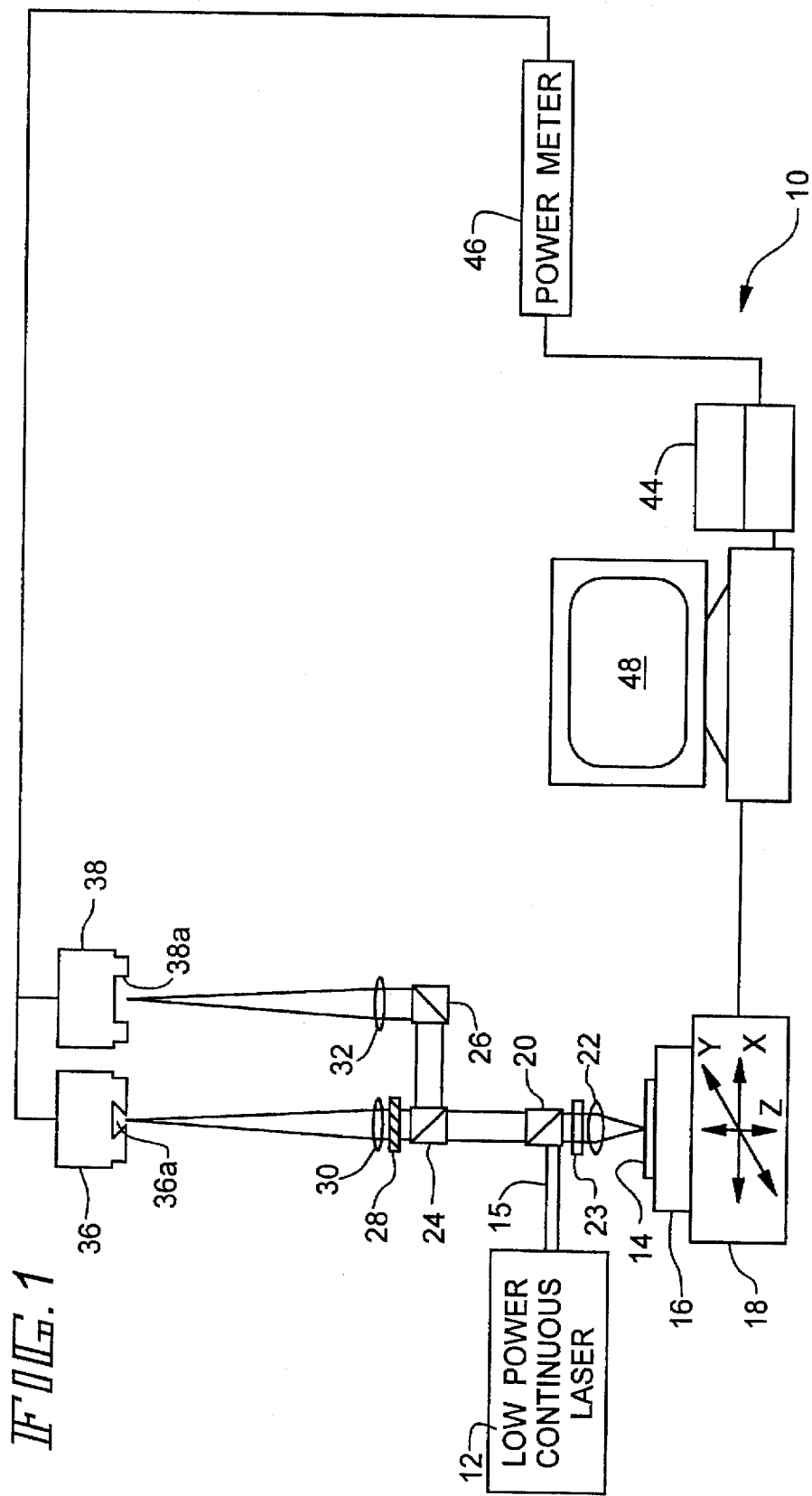
FIG. 1 is a simplified, combined block and schematic diagram of a detection system for the automatic, real-time detection of defects during the machining of ceramics in accordance with the present invention.

Referring to FIG. 1, there is shown a simplified combined block and schematic diagram of an automated real-time defect detection system 10 in accordance with the principles of the present invention. The automated real-time defect detection system 10 employs two detectors which acquire the integrated light intensity in a central region and in the perimeter region of the scattering light and provide a two dimensional scatter image of a ceramic specimen by scanning its surface.

A low power, continuous laser beam source 12 directs a laser beam 15 onto a ceramic component 14. In the disclosed embodiment, laser beam source 12 is a 10 mW He-Ne laser. Laser beam 15 is initially directed through a first surface-illuminating polarizing beam-splitter (PBS) cube 20 and thence onto the surface of the ceramic component 14 via a first focusing lens 22. The first focusing lens 22 is representative of the focussing optics used in the automated real-time defect detection system 10 for the purpose of removing or reducing the effects of ceramic component surface curvature, with the specific optical focussing elements employed dictated by the shape of the ceramic component 14. If subsurface inspection of the ceramic component is desired, no additional optics are required in the illumination optical path. Light reflected from the surface of the ceramic component 14 will not undergo a change in polarization unless the surface is extremely rough. Therefore, all surface-scattered light will again be reflected by the first PBS cube and directed toward the laser beam source 12. However, any light that is scattered from the subsurface of the ceramic component 14 undergoes several reflections and refractions at the grain boundaries, with each of these reflections and refractions serving to alter the light's polarization. The net affect of this behavior is to randomize the polarization of the subsurface scattered light and render the scattered light completely diffuse. Thus, part of the subsurface-scattered light will also be reflected by the first PBS cube 20 and directed back to the laser beam source 12, while the other part of the subsurface-scattered light will be transmitted by the first PBS cube along a detection light path. If surface-scattered light is of interest, a properly oriented quarter-wave ($\lambda/4$) plate 23 may be inserted between the first PBS cube 20 and the surface of the ceramic component 14. This serves to rotate the light's polarization by 90° on each pass. Because the light passes through the $\lambda/4$ plate 23 twice (once in illumination, once in reflection), the net effect is to delay the phase 180° or rotate its polarization 90°, thereby changing vertical polarization to horizontal and visa versa. Therefore, with the $\lambda/4$ plate 23 in place, all of the surface-scattered and part of the subsurface-scattered light is transmitted to the detection path, while the other part of the subsurface scatter is directed back toward the laser 12. Because the surface-scattered light is usually much more intense than the subsurface-scattered light, it dominates the detected signal so that the subsurface scatter can be neglected.

The ceramic component 14 is shown coupled to and supported by a support platform 16. Support platform 16 may take various forms including a lathe as described in greater detail below. For purposes of the present explanation, the ceramic component 14 is shown as simply attached to and supported by a support platform 16. Support platform 16 is, in turn, coupled to a translation/rotation stage 18 for rotationally as well as translationally displacing the ceramic component 14 so that its entire surface and near-surface portions can be analyzed for defects by the automated real-time defect detection system 10 of the present invention.

The portion of the laser beam reflected from the ceramic component 14 which is not reflected back to the laser beam source 12 is transmitted via the first PBS cube to a second PBS cube 24. The second PBS cube 24 transmits half of the light reaching it along a first detection path and reflects the other half of the light reaching it along a second detection path. Disposed along the first detection path is the combination of a quarter-wave ($\lambda/4$) plate 28, a second focussing lens 30 and a detector 36 with a pinhole aperture 36a. Disposed along the second detection path is a third PBS cube 26, a third focusing lens 32 and a second detector 38 with a wide aperture 38a.

The second focussing lens 30 is a positive lens for forming an image on the polished stainless steel pinhole aperture 36a which is preferably on the order of 100 μm in diameter in the first detector 36. Therefore, any light which is scattered from the subsurface of the ceramic component 14 directly beneath the spot of the incident laser beam passes through the pinhole aperture 36a and onto the first detector 36. The remaining light that is scattered from the area around the illuminating laser beam spot on the ceramic component 14 is reflected back through the first focussing lens 22 and onto the second PBS cube 24. In the latter case, the polarization of the reflected laser light has been rotated to horizontal and it is reflected by the second PBS cube 24 and is directed to a 50/50 beam splitter 26. One side of the 50/50 beam splitter 26 is imaged by a third positive focussing lens 32 onto a second detector 38 having a wide aperture 38a. The light scattered from the area around the illuminating laser beam spot on the ceramic component is thus directed to the second detector 38.

By monitoring the sum of the outputs of the first and second detectors 36, 38, i.e., A+B, the total back-scattered intensity can be measured. This sum will be most indicative of lateral defects. As the laser illumination is rastered across the surface of the ceramic component 14 or the ceramic component is raster scanned below the laser beam, these sum values are assembled into a gray-scale image of the surface, heretofore referred to as the "sum" image. However, if the ratio of outputs from the first and second detectors 36, 38, i.e., B/A, is computed, an indication of the degree of lateral spread of the subsurface scatter is obtained. This value will primarily be sensitive to median defects. Again, as the ceramic component 14 is scanned by the laser beam 15, these ratio values are assembled into a gray-scale image heretofore referred to as the "ratio" image. Most real defects near or on the surface of the ceramic component 14 will have some orientation between median and lateral, and will therefore provide an indication in each of the sum and ratio images, though one image will often dominate over the other.

The outputs of the first and second detectors 36, 38 are provided via a power meter 46 to a computer controller 44. Computer controller includes a video display 48 for providing a video image of a light scattering defect on or near the surface of the ceramic component 14. Computer controller 44 synchronizes the displacement of the translation/rotation stage 18 and the movement of the ceramic component 14 with the rate at which data is acquired from the first and second detectors 36, 38 as well as with the rate data is provided to the video display 48 for the presentation of a video image of a defect. The automated real-time defect detection system 10 of the present invention, provides information on the location, size, type and relative severity of surface and near subsurface defects in the ceramic component 14.

Referring to FIG. 2, there is shown a simplified schematic diagram of a translation/rotation stage 60 for the machining of a ceramic tensile rod 64 for use with the automated real-time defect detection system of the present invention. The translation/rotation stage 60 includes a lathe 66 which engages and supports the ceramic tensile rod 64. Lathe 66 is powered by an electric motor 68 and is, in turn, positioned on and supported by a translation stage 70 which includes a linear track 72. Lathe 66 rotates the ceramic tensile rod 64, while the translation stage 70 provides for the linear displacement in the direction of arrow 71 of the ceramic tensile rod relative to a laser beam 62 incident upon the surface thereof. In the described embodiment, a grinding wheel 78 machines the surface of the ceramic tensile rod 64 as it undergoes rotation and translation. The present invention, however, is not limited to use with a grinding wheel, but may be used with virtually any surface machining tool. The drive mechanism for the grinding wheel is conventional in design and operation, and is thus not shown in the figure for simplicity. The cutting fluid and swarf adjacent the spot of incidence of the laser beam 62 on the ceramic tensile rod 64 is cleared from the ceramic component by an air blast provided by a pressurized air source 74 via an air tube 76 which terminates adjacent the surface of the ceramic tensile rod. As the cylindrical ceramic tensile rod 64 is rotated and axially translated, its surface is continuously scanned by the incident laser beam 62 of the elastic optical scattering system to obtain two-dimensional images on the aforementioned video display in real-time of any defects imparted in the ceramic tensile rod 64 by the grinding wheel 78 as they occur. By having known "feature masks" representing categories of defects stored in the aforementioned computer controller 44 shown in FIG. 1, defects detected by the automated real-time detection system of the present invention may be automatically characterized. Where the ceramic specimen is only rotated and not translated in the axial direction, the optical system including the source of laser beam 62 may be translated by a linear stage similar to that shown in FIG. 2 to obtain the scanned images of defects on or near the surface of the ceramic specimen.

Figures 4A, 4B, 4C:
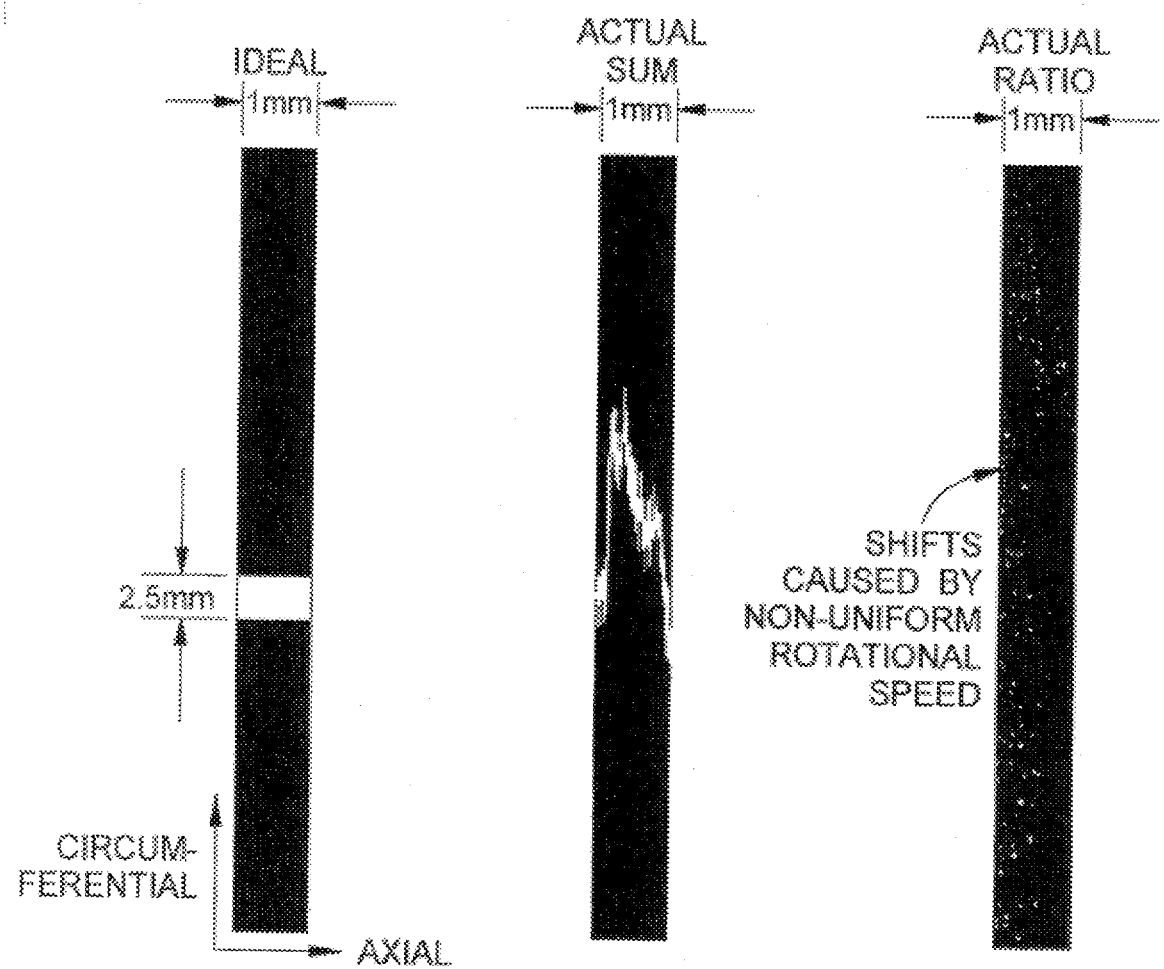
FIGS. 4a, 4b, and 4c respectively show the ideal, actual sum, and actual ratio images of the portion of the tensile rod shown in FIG. 3 scanned by a laser beam for the detection of defects in accordance with the present invention.

Referring to FIG. 3, there is shown a side elevation view of a ceramic tensile rod 52 showing a portion of the rod in the form of a 1 mm area 52a which is scanned by a laser beam as the rod is rotated in accordance with the present invention. A defect on the surface of the rod 52 is represented by a 2.5 mm wide strip of paper 52b disposed on the ceramic tensile rod 52 over a portion of the laser scanned area 52a. Referring to FIG. 4a, there is shown an ideal image of the 2.5 mm wide strip of paper 52b shown in FIG. 3 as detected by the automated real-time defect detection system of the present invention. Referring to FIG. 4b, there is shown an actual measured dynamic elastic optical scattering sum image showing the detected surface marker as an irregular line. Similarly, FIG. 4c shows a dynamic elastic optical ratio image of the 2.5 mm wide strip of paper 52b on the tensile rod 52 of FIG. 3 as detected by the automatic real-time defect detection system of the present invention. The image shifts shown in FIGS. 4b and 4c are caused by the non-uniform rotational speed of the tensile rod 52.

Figure 5A:
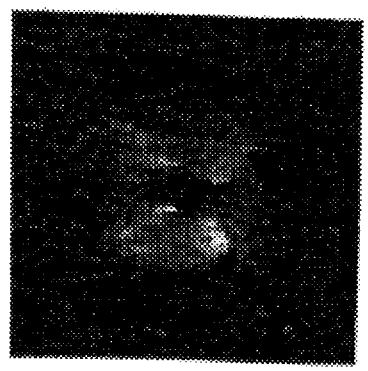
FIGS. 5a and 5b are images of a Vickers indent respectively showing a sum image (lateral defect) and a ratio image (median defect) in a 0.05 mm square as detected and recorded by the present invention.
Figure 5B:
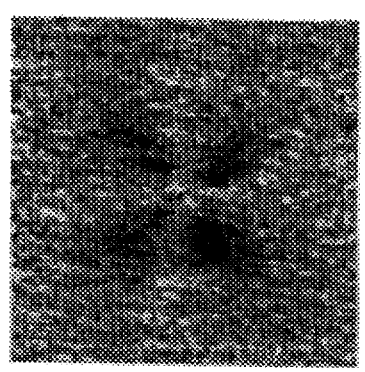

Referring to FIGS. 5a and 5b, there are respectively shown the laser scatter sum and ratio images of a median crack introduced in an $Si_3N_4$ (NT164) flexure bar using Vickers indents as detected and displaced by the automated real-time defect detection system of the present invention. The elastic optical summing image illustrated in FIG. 5a shows two types of cracks. First, the lateral "cone-type" cracks indicated by a brighter "halo" around the indent emanate beneath the surface from the indent. Second, the median cracks can also be seen in FIG. 5b as extending from the corners of the indents with the lower right crack being most severe because the cracks are not perfectly straight so that they have a lateral component. In addition, the actual surface indent is visible in the sum image of FIG. 5a as a darker region near the indent center. By comparison, the median defect image of FIG. 5b shows no indication of the lateral defects and is almost completely insensitive to the actual surface indent itself. Rather, the median defect image of FIG. 5b is only an indication of the presence of the median cracks extending from the indents' corners. Although these corner cracks are also shown in the sum image of FIG. 5a, because they are not perfectly normal to the surface, their signature is substantially reduced. Although the ratio image of FIG. 5b shows that the cracks extend well beyond the corners of the indent, the indication becomes weaker at the crack ends, indicating a smaller crack depth, because a smaller crack depth represents an increasingly smaller fraction of the total optical penetration depth. Two diamond ground $Si_3N_4$ (GS-44) coupons were analyzed by the automated real-time defect detection system of the present invention for machining-induced subsurface defect detection. The coupons were about 25 mm square in size and the machining conditions used are listed in Table 1.

TABLE 1

| Coupon ID | 10102 | 10202 |
| --- | --- | --- |
| Wheel grit number | 80 | 320 |
| Surface wheel speed (m/s) | 35 | 74 |
| Down feed (mm) | 0.018 | 0.018 |

The specimen 10102 shown in FIGS. 6a and 6b was ground with coarse grit size but low grinding speed, whereas specimen 10202 shown in FIGS. 7a and 7b was ground with finer grit size but at a high grinding speed. Six surface areas of 1.28×6 mm² each with a resolution of 10 μm were scanned on each of the specimens. FIGS. 6a and 6b respectively show the ratio and sum images for the specimen coupon 10102, while FIGS. 7a and 7b respectively show the ratio and sum images of the specimen coupon 10202. The machining direction or lay direction is vertical in the illustrated images. In the sum images, the white speckles represent surface regions with excessive light scattering which is due to subsurface defects or cracks. Correspondingly, the damaged regions are shown as dark speckles in the ratio images. The ratio and sum images respectively shown in FIGS. 6a, 7a and 6b, 6b are sensitive respectively to the median and lateral cracks in the specimen subsurface.

Figure 8A:
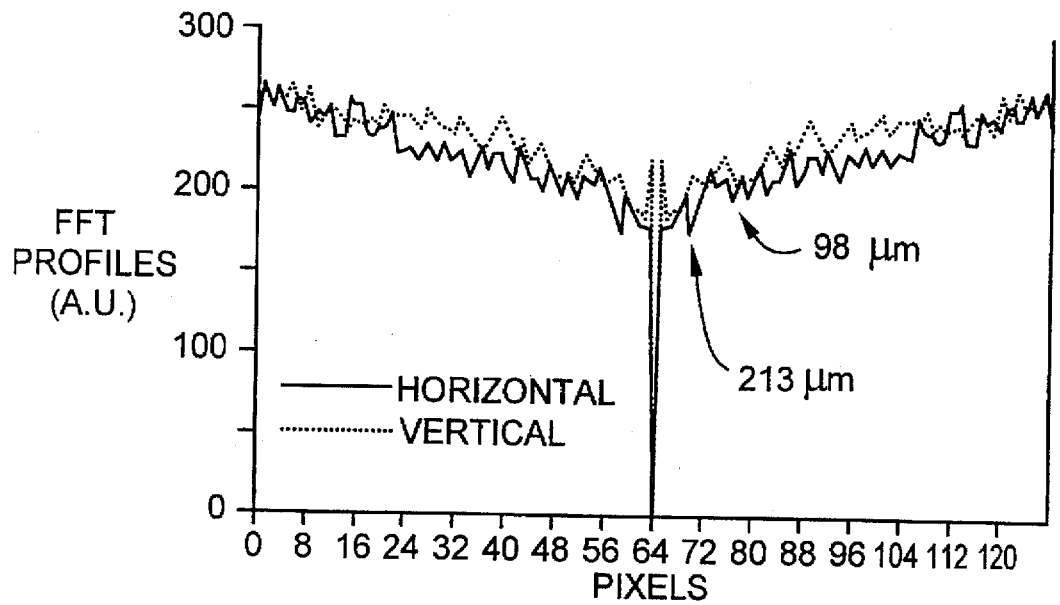
FIGS. 8a and 8b are graphic representations of the averaged Fast Fourier Transform (FFT) profiles of scattering ratio images of the $Si_3N_4$ (GS-44) coupon 10102 and the $Si_3N_4$ (GS-44) coupon 10202, respectively.
Figure 8B:
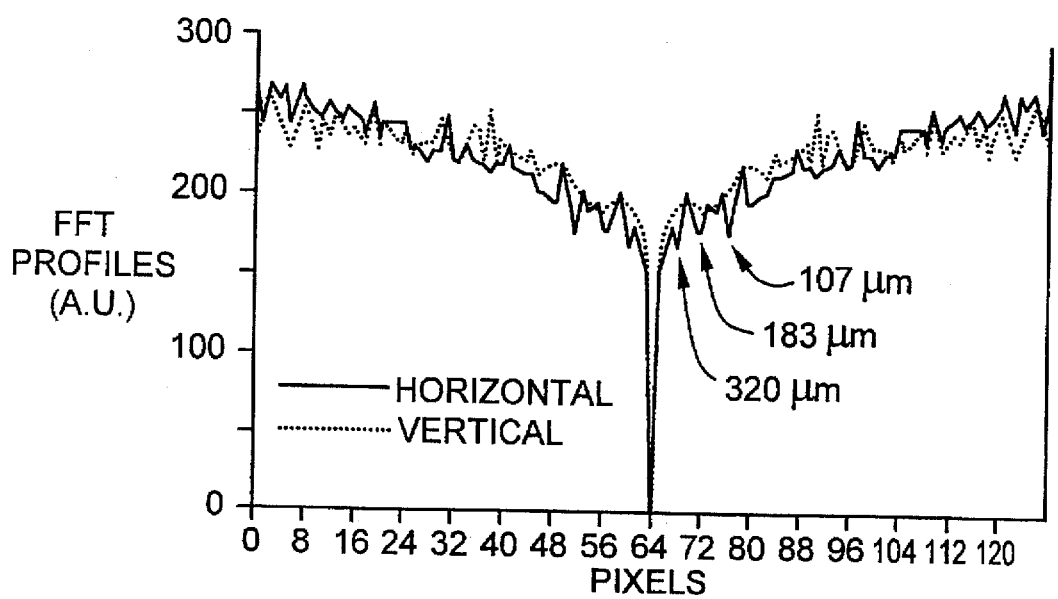

Two types of machining-induced damage are visible from these images. First, machining marks are represented by vertical lines, darker lines in ratio images and whiter lines in sum images. These marks are most likely the median cracks generated when the grinding particles pass through the specimen surfaces. Second, individual damaged areas, or individual speckles, are distributed all over the specimen subsurfaces. The scattering images in FIGS. 6a, 6b and 7a, 7b show different speckle patterns between the two specimens. The frequency of these speckles can be found from the Fast Fourier Transform (FFT) of the images. However, as the FFT images displayed in gray scales are difficult to extract quantitative information from, only the central horizontal and vertical profiles of the 2-D FFT images are plotted and shown in FIGS. 8a and 8b, which are graphic representations of the averaged FFT profiles of scattering ratio images of the $Si_3N_4$ (GS-44) coupon 10102 and the $Si_3N_4$ (GS-44) coupon 10202, respectively. These figures illustrate the averaged FFT profiles from the scattering ratio images at all six locations on the two specimens. The horizontal direction is across the lay and the vertical is along the lay on the specimen. The central spike at pixel 64 in the profiles represents the zero frequency and the frequency increases toward both sides. It is seen that lower frequency components are generally dominant. The speckles across the lay direction in specimen 10102 have a dominant spatial period (inverse of frequency) at about 213 μm while those in specimen 10202 have a dominant spatial period at 320 μm. In FIG. 8a, by comparing the horizontal profile to the vertical profile, it can be seen that the 213 μm period exists only in the horizontal direction (across the lay). Similarly, in FIG. 8b the 320 μm and 107 μm periods are present only in the horizontal direction. If we assume an isotropic distribution of the individual speckles, these periods then correspond to those of the machining marks. The additional characteristic frequencies that are present in both the horizontal and vertical profiles are likely attributed to by the distributed individual speckles. Therefore, by analyzing the FFTs of the scattering images, the differences of the suspected machining-induced damage in the two directions may be characterized.

There has thus been shown a novel, noncontact, nondestructive automated real-time defect detection system employing elastic optical scattering to detect defects and/or damage in the surface and subsurface portions of ceramic materials. The technique is based on the unique property of ceramics to partially transmit visible (and infrared) light into a subsurface. Using polarization techniques, the effects of surface and subsurface defects to depths of several hundred micrometers can be distinguished. The detection system employs two detectors for detecting both lateral and median type defects in the material subsurface by measuring both the back-scattered light intensity and the lateral spread of scattered light. Through the application of a two-dimensional scanning system, conformally mapped images of the scattering surface or subsurface can be generated with specified resolutions. The automated real-time defect detection system was used to detect defects and/or damage in both test specimens and actual machined components of several different $Si_3N_4$ ceramic materials. The types of defects that were detected included surface spalls simulated by Vickers indents, C and Hertzian surface-breaking cracks, subsurface lateral and median cracks simulated by machined step-wedges as well as real C-cracks and cracks generated by Vickers indents, subsurface porosity as simulated with back-surface drilled holes and real porosity variation produced by the manufacturing process, subsurface anisotropy created by uniaxial pressing, subsurface RCF damage and diamond-grinding-induced damage. The results show that the laser scattered technique is capable of detecting and identifying different types of surface and subsurface defects that are critical to component strengths and lifetimes. The laser scatter technique is employed in the defect detection system of the present invention to provide an automated real-time capability to detect various types of defects induced in the ceramic body during machining. Laser light is directed onto the newly machined surface, with the cutting fluid and swarf near the light spot cleared by an air blast. For the case of a cylindrical ceramic specimen, as it is rotated and axially translated, its surface is continuously scanned by the elastic optical scattering system to obtain two-dimensional images of the surface and subsurface defects.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. Apparatus for the detection and display of surface and near-surface defects in a ceramic body during machining of a surface of said ceramic body, wherein various types of defects may be introduced in a surface and near-surface portion of said ceramic body during said machining, said apparatus comprising:

a light source for providing a polarized laser beam;

optical means for focussing and directing said polarized laser beam onto the surface of the ceramic body;

displacement means for providing relative displacement between the ceramic body and said light source whereby said polarized laser beam scans the surface of the ceramic body;

a plurality of detectors responsive to said polarized laser beam reflected from the surface and near-surface portions of the ceramic body for detecting various types of surface and near-surface defects in the ceramic body; and display means coupled to said plurality of detectors for providing a video image of said various types of surface and near-surface defects in the ceramic body.

2. The apparatus of claim 1 wherein said plurality of detectors includes a first detector for receiving light scattered from a subsurface of the ceramic body directly beneath a location of incidence of said laser beam on the ceramic body for providing a first output and a second detector for receiving light scattered from an area around the location of incidence of said laser beam on the ceramic body for providing a second output.

3. The apparatus of claim 2 wherein said first detector includes a pinhole aperture through which light scattered from said subsurface of the ceramic body directly beneath the location of incidence of said laser beam on the ceramic body is detected.

4. The apparatus of claim 2 wherein said first and second outputs of said first and second detectors are added together to provide a third output representing a total intensity of the light reflected from the ceramic body, and wherein the total intensity of the reflected light is representative of lateral defects in the ceramic body.

5. The apparatus of claim 2 wherein said first output is divided by said second output to form a ratio of said outputs, and wherein the ratio of said outputs is representative of median defects in the ceramic body.

6. The apparatus of claim 1 wherein said light source includes a low powered, continuous He-Ne laser.

7. The apparatus of claim 1 wherein said optical means includes a combination of a polarizing beam-splitter cube and a focussing lens.

8. The apparatus of claim 7 wherein said optical means further includes a plurality of polarizing beam-splitter cubes and focussing lenses.

9. The apparatus of claim 7 wherein said optical means further includes at least one ¼ wavelength plate disposed intermediate a polarizing beam splitter cube and a focussing lens.

10. The apparatus of claim 1 further comprising means for removing foreign material produced during machining of the ceramic body from the surface of the ceramic body.

11. The apparatus of claim 10 wherein said means for removing foreign material includes a source of pressurized air and an air tube having an end portion disposed adjacent a portion of the surface of the ceramic body where said laser beam is incident thereon.

12. The apparatus of claim 1 wherein said displacement means includes a lathe for providing rotational relative displacement between the ceramic body and said light source.

13. The apparatus of claim 12 wherein said displacement means further includes a translation stage for providing linear relative displacement between the ceramic body and said light source.

14. The apparatus of claim 1 further comprising controller means for synchronizing the relative displacement between the ceramic body and said light source with a rate at which video information is presented on said display means.

15. The apparatus of claim 1 further comprising means for comparing defects detected in the ceramic body with feature masks representing categories of defects for automatically classifying the defects detected in the ceramic body.

* * * * *

UNITED STATES PATENT AND TRADEMARK OFFICE
CERTIFICATE OF CORRECTION

PATENT NO. : 5,689,332
DATED : November 18, 1997
INVENTOR(S) : William A. Ellingson, et al.

It is certified that error appears in the above-identified patent and that said Letters Patent is hereby corrected as shown below:

Title page,

Item [56], References Cited, U.S. Patent No. "4,933,537", should be --4,933,567--.

Item [56], Other Publications, "Analytical" should be --Analytic--.

Signed and Sealed this

Nineteenth Day of May, 1998

Attest:

BRUCE LEHMAN

Attesting Officer

Commissioner of Patents and Trademarks